United States Patent
Wells et al.

[11] Patent Number: 5,113,886
[45] Date of Patent: May 19, 1992

[54] APPARATUS FOR WASHING MAGNETIC PARTICLES IN A VESSEL WITH A BOTTOM PULL

[75] Inventors: John R. Wells, Culver City; Jack R. Uren, Jr., Seal Beach, both of Calif.

[73] Assignee: Source Scientific Systems, Inc., Garden Grove, Calif.

[21] Appl. No.: 521,246

[22] Filed: May 8, 1990

[51] Int. Cl.$^5$ .................................................. B08B 3/02
[52] U.S. Cl. .................................. 134/172; 134/167 R
[58] Field of Search ........... 134/166 R, 167 R, 168 R, 134/169 R, 167 C, 168 C, 172, 24; 15/302, 304; 239/124, 125, 126, 127; 137/577, 592; 141/65, 91, 92; 201/2; 202/241; 208/48 R; 366/134, 137

[56] References Cited

U.S. PATENT DOCUMENTS

| | | | |
|---|---|---|---|
| 4,053,284 | 10/1977 | Posch | 134/167 R X |
| 4,635,665 | 1/1987 | Namba et al. | 134/167 R |

FOREIGN PATENT DOCUMENTS

| | | | |
|---|---|---|---|
| 522657 | 4/1921 | France | 366/134 |
| 783947 | 10/1957 | United Kingdom | 366/137 |

*Primary Examiner*—Philip R. Coe
*Attorney, Agent, or Firm*—Donald G. Lewis

[57] ABSTRACT

An apparatus for washing pellets of magnetic particles magnetically bound to the bottom of a test tube employs a liquid handling probe having an aspiration channel with a forked inlet for positioning the probe onto the periapical region of the test tube for optimizing both the aspiration and expression of liquids. While contacting the periapical region of the test tube, the forked inlet may aspirate liquid adjacent to the pellet without contacting the magnetic particles. Furthermore, the contact between the forked inlet and the periapical region of the test tube, serves to position the outlet of the liquid channel directly over the pellet for dislodging and resuspending the magnetically bound pellet with a forceful stream of wash liquid.

7 Claims, 3 Drawing Sheets

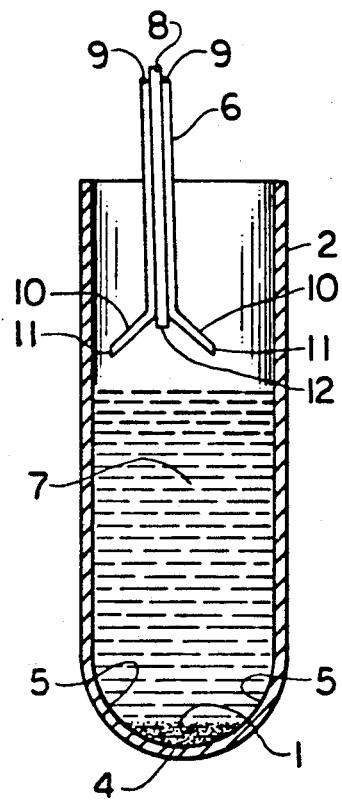
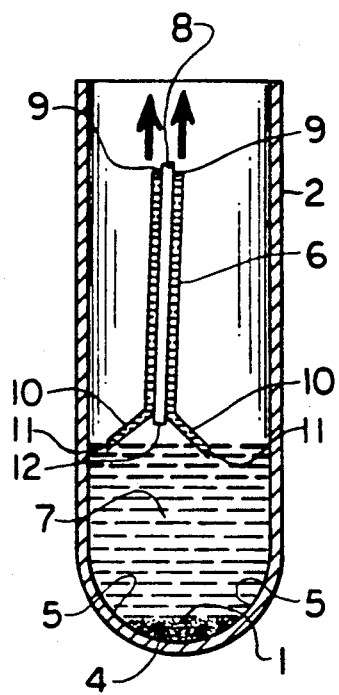
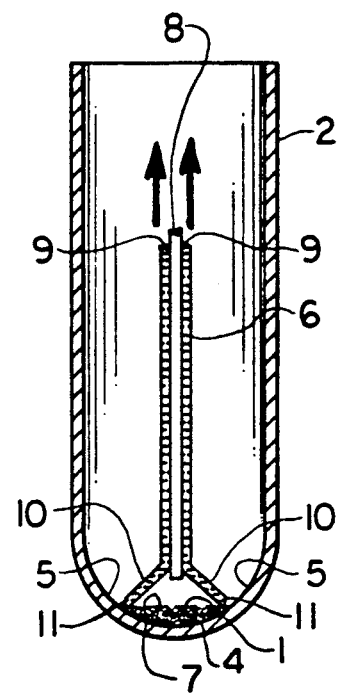
FIG. 3    FIG. 4    FIG. 5
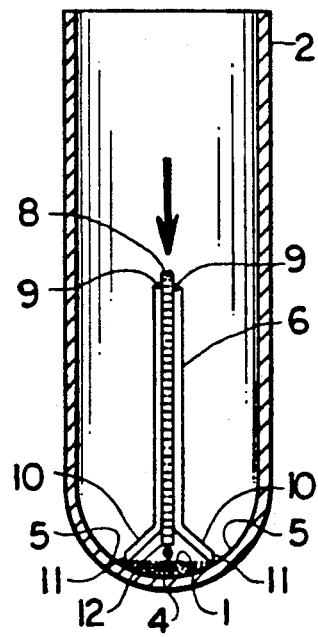
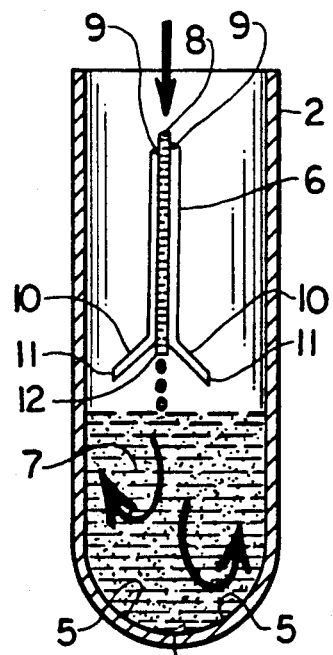
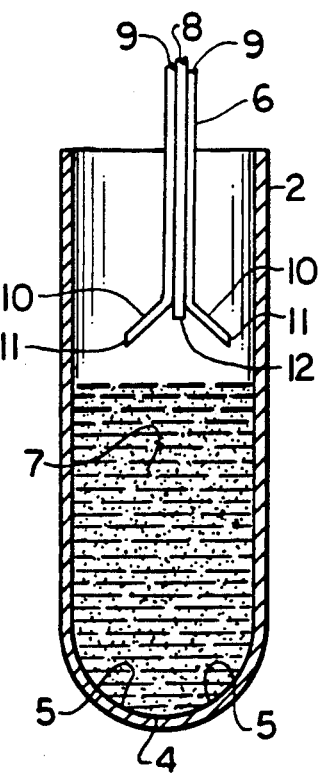
FIG. 6    FIG. 7    FIG. 8

APPARATUS FOR WASHING MAGNETIC PARTICLES IN A VESSEL WITH A BOTTOM PULL

BACKGROUND

The invention relates to devices for washing magnetic particles. More particularly, the invention relates to devices for washing magnetic particles in conjunction with a magnetic bottom pull.

A suspension of magnetic particles coated with antibodies or other binding reagents may be employed as a versatile solid phase for separating a variety of soluble or suspendable entities, including various analytes, antigens, and cells. After a suspension of magnetic particles has bound its target entity, the application of a magnetic field causes the magnetic particles to migrate to the area of greatest field density. This process is called magnetic sedimentation. The magnetic particles form a pellet in the area of greatest magnetic field density. As the magnetic particles sediment toward their pellet, they carry their target entities with them.

One protocol for magnetic separation employs a test tube rack having a magnet positioned at the bottom. The magnet is oriented so that, when test tubes are inserted into the rack, the magnetic particles magnetically sediment to the bottom of the tube. This orientation of magnet is called a bottom pull. After the magnetic particles have formed a pellet, the test tube rack is inverted so as to cause the liquid phase to decant from the test tubes. During the decanting process, the pellet of magnetic particles is retained within the test tube by magnetic attraction. After the liquid is decanted, wash liquid may be pipetted into the test tube. The test tube is then vortexed in order to resuspend the magnetic particles into the wash liquid. After the vortexing, the test tube may be reinserted into the magnetic rack so as to cause the resuspended magnetic particles to magnetically sediment a second time. After the magnetic particles have pelleted, the wash liquid may be decanted so as to complete one wash cycle. Further wash cycles may be performed as required Since the magnet is relatively heavy, the process of tilting the rack when decanting the test tube can be somewhat cumbersome. Also, since each test tube must be vortexed manually, the resuspension process can become somewhat tedious. Accordingly, what was desired was a method for evacuating the test tube without titling the rack and for resuspending the magnetic particles without vortexing or removing the test tubes from the magnetic rack.

SUMMARY

The invention is a forked liquid handling probe for washing magnetic particles in conjunction with a bottom pull. The invention is employed to wash magnetic particles which have magnetically sedimented and pelleted onto the lowest point of the test tube, i.e. the apical region. The probe serves both to aspirate liquid and to express liquid. The probe may be inserted into the test tube by means of an X-Y-Z positioner. The forked probe includes two or more prongs which serve to center the probe over the pellet, i.e. over the apical region. As the probe is inserted into the test tube, the prongs eventually contact the periapical region of the test tube, i.e. the region immediately surrounding the apical region. The periapical region has a generally conical shape. The contact between the prongs and the periapical region causes the probe to center itself over the apical region. The prongs may include vacuum channels with inlets at the extremity of each prong for aspirating or evacuating the liquid as the probe is lowered into the test tube. Inlets at the extremity of the probes contact the periapical region and serve to aspirate liquid proximate to the pellet without actually contacting the pellet. The probe also includes a liquid channel for expressing liquid into the test tube. The liquid channel opens onto an outlet which is centered between the prongs so that it sits directly over the center of the apical region, i.e. the pellet. After the liquid has been aspirated from the tube, the pellet may be resuspended by expressing wash liquid with force directly down on the pellet. As liquid enters the test tube, the probe may be slowly elevated by the X-Y-Z positioner so as to avoid contact between the probe and the rising liquid level or miniscus.

After the resuspension is complete, the magnetic particles may repellet and the wash liquid aspirated once again as described above.

BRIEF DESCRIPTION OF THE DRAWINGS

FIGS. 3-8 are sectional view of the test tube and probe of FIG. 1 illustrating the sequence for washing the magnetic particles.

FIG. 3 illustrates the test tube with a pellet of magnetic particles and prewash liquid.

FIG. 4 illustrates the prewash liquid being aspirated as the probe is lowered into the test tube.

FIG. 5 illustrates the completion of the aspiration step and the centering of the prongs of the forked probe over the pellet by its contact with the periapical region of the test tube.

FIG. 6 illustrates the commencement of the dislodging and mixing of the pellet by the expression of wash liquid.

FIG. 7 illustrates the continuation of the addition of wash liquid to the test tube.

FIG. 8 illustrates the completion of the resuspension of the magnetic particles within the wash liquid.

DETAILED DESCRIPTION OF THE INVENTION

The Apparatus

Figure 1:
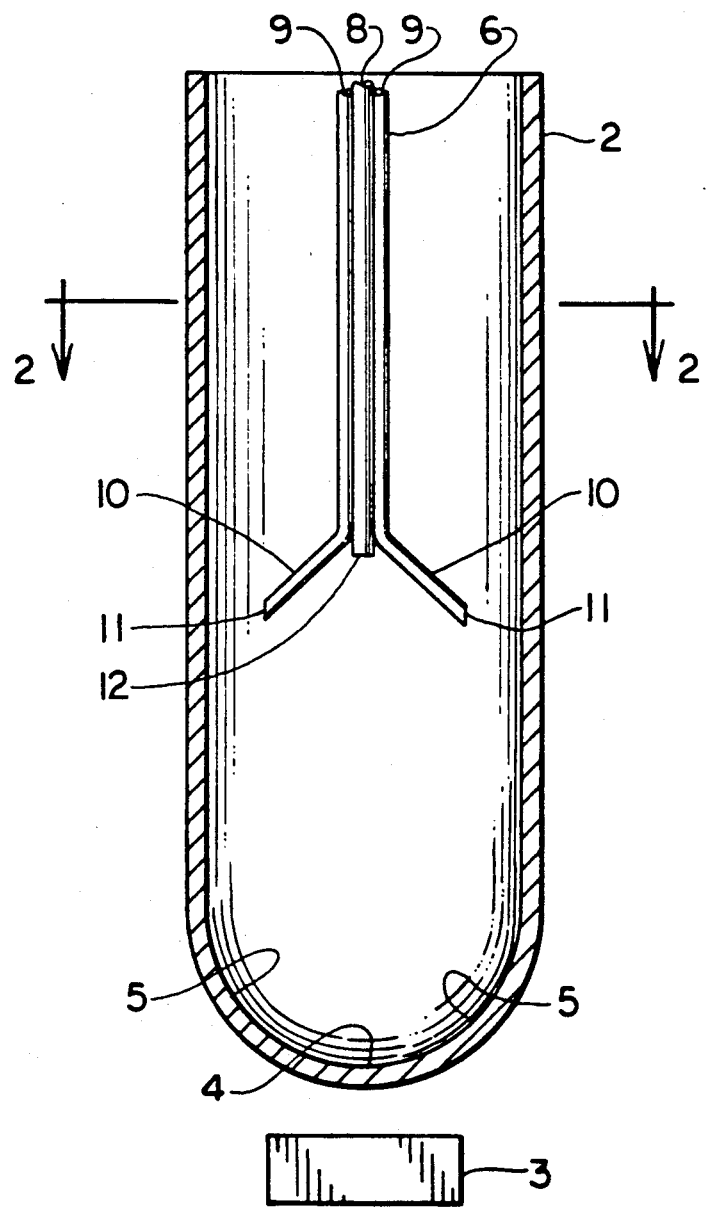
FIG. 1 a schematic view of a bottom pull magnet and sectional views of a test tube vessel and a fragment of a probe therein.
Figure 2:
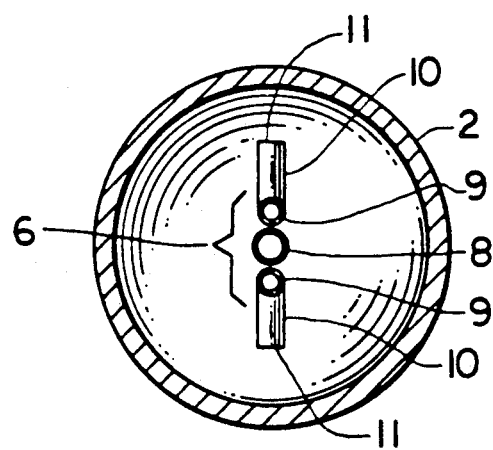
FIG. 2 is a sectional view of the test tube and probe of FIG. 1 viewed from above.

The invention is employed for washing magnetic particles (1). More particularly, the invention is employed for washing magnetic particles (1) which have been magnetically sedimented within test tubes (2) or other vessels mounted in a magnetic rack having a bottom pull (3). The magnet (3) in a rack having a bottom pull configuration draws the magnetic particles (1) to the bottom of the test tube (2). In particular, the magnet (3) draws the particles (1) to the apical region (4) of the test tube (2), i.e. the lowest point within the test tube (2). Surrounding the apical region (4) is a periapical region (5). The periapical region (5) has a generally hemispherical or conical shape. When sedimenting magnetic particles (1) contact the periapical region (5), they will continue to be drawn by the magnet (3) and will slide centripetally toward the apex of the cone, i.e. the apical region (4). Hence, once the sedimentation process is complete, the periapical region (5) is largely free of pelleted magnetic particles (1). A pellet of magnetic particles (1) will be magnetically bound to the apical region (4).

The invention utilizes the geometry of the hemispherical or conical shape of the periapical region (5) for centering the probe (6) within the best position for dislodging and resuspending the pellet and for avoiding contact between the pellet material and the probe (6) while aspirating liquid (7) from the test tube (2).

The probe (6) includes a liquid channel (8) and a vacuum channel (9). In the preferred embodiment, both the liquid channel (8) and the vacuum channel (9) are cylindrical in shape and have a composition of metal or high strength plastic. The liquid channel (8) and the vacuum channel (9) are parallel or adjacent to one another and are mechanically coupled so that they move in unison with one another.

The probe (6) includes a forked portion having two or more prongs (10). When the probe (6) is inserted into a test tube (2), the forked portion is at the leading end of the probe (6). When the probe (6) contacts the bottom of the test tube (2), the prongs (10) contact the periapical region (5). The prongs (10) have a span which exceeds the span of the apical region (4), i.e. the region to which the pellet is magnetically bound. Indeed, the span of the prongs (10) is sufficiently large so that they can not contact the apical region (4). In the preferred embodiment, after the probe (6) contacts the bottom of the test tube (2), it is sufficient force is applied to the probe (6) by spring action or other biasing means so that the prongs (10) slide to their lowest position within the periapical region (5). This sliding action causes the probe (6) to be position directly over the apical region (4), i.e. the pellet.

In the preferred mode, the vacuum channel (9) serves as the forked portion. The vacuum channel (9) branches with two or more forked inlets (11) to form the forked portion. In the preferred embodiment, the inlets (11) contact the periapical region (5). When the forked inlets (11) are pressed onto the periapical region (5) so as to center the probe (6) over the pellet, the forked inlets (11) slide to the lowest position within the periapical region (5) and achieve the optimal position to evacuate the test tube (2) without contacting or disturbing the pellet. In the preferred embodiment, the vacuum channel (9) consists of two or more subchannels. A probe (6) having two vacuum subchannels is illustrated in FIG. 1. The vacuum channel (9) on the left serves as a first subchannel; the vacuum channel (9) on the right serves as a second subchannel. Each subchannel is bent near its terminus to form the forked inlets (11). Alternatively, a single vacuum channel (9) may be employed with the forked inlets (11) being joined thereto and branching therefrom.

The liquid channel (8) is mechanically coupled with the vacuum channel (9) so that when the forked inlets (11) are centered with respect to the apical region (4), the outlet (12) for the liquid channel (8) is positioned directly over the pellet, i.e. the apical region (4). The liquid channel (8) serves to express liquid (7) directly onto the pellet so as to dislodge and resuspend the magnetic particles (1). The outlet (12) for the liquid channel (8) has a length such that, when the probe (6) is center over the pellet by means of the contact between the forked inlets (11) and the periapical region (5), the outlet (12) extends to a position which is short of the pellet material, i.e. the outlet (12) avoids contact with the pellet material. Accordingly, the length of the outlet (12) will depend upon the geometry of the test tube (2) and of the forked inlets (11) and of the quantity of magnetic particles (1) which comprise the pellet.

In the preferred embodiment, a plurality of probes (6) of the type described above are employed with a manifold type liquid handling apparatus similar to the apparatus described by Namba et al, U.S. Pat. No. 4,635,665, incorporated herein by reference. The apparatus includes two manifolds, viz. a dispensing manifold and an aspirating manifold. The dispensing manifold is connected to a liquid source for charging the dispensing manifold with liquid (7). The aspirating manifold is connected to a vacuum source for evacuating the aspirating manifold. Connected to the dispensing manifold is a plurality of liquid channels (8). Activation of the liquid source first causes the charging of the dispensing manifold then causes the expression of liquid (7) from each of the outlets (12) of the plurality of liquid channels (8). Connected to the aspirating manifold is a plurality of vacuum channels (9). Activation of the vacuum source first causes the evacuation of the aspirating manifold then causes the aspiration of liquid (7) into each of the inlets (11) of the plurality of vacuum channels (9). In the preferred mode, each of the various channels are siphoned shaped and attach to the top of their respective manifolds.

The plurality of probes (6) emanating from the manifolds is organized into an array which matches or complements the geometry of the array of test tubes (2) which are mounted in the magnetic rack. Accordingly, the array of probes (6) may be inserted into the array of test tubes (2) with one motion.

The apparatus may also include an X-Y-Z positioner or other vertical and/or horizontal translating means for vertically and/or horizontally translating the array of probes (6). Horizontal translation may be employed for washing a series of racks of test tubes (2). Vertical translation of the probes (6) is employed during the washing method.

The Method

The apparatus and probes (6) described above may be employed within a method for washing pelleted magnetic particles (1). In particular, the magnetic particles (1) should be pelleted with a bottom pull (3) which draws the magnetic particles (1) to the apical region (4) of the test tube (2).

Conventionally, magnetic particles (1) are employed for separating a bindable component from unbound components. A suspension of magnetic particles (1) is incubated with the bindable component. The suspension is then magnetically pelleted. The unbound components remain within the prewash liquid (7) and require removal from the pelleted magnetic particles (1).

Accordingly, after the magnetic sedimentation is complete, the prewash liquid (7) may be removed by application of the probe (6). The probe (6) is initially inserted into the top of test tube (2), fork first. The probe (6) is then translated vertically downward into the vessel while simultaneously activating the vacuum source. Activation of the vacuum source cause prewash liquid (7) to be aspirated into the forked inlets (11) as the probe (6) is translated downwardly. In the preferred mode, the rate of aspiration is sufficiently greatly so that the inlets (11) remain near the meniscus of the prewash liquid (7) as both the meniscus and the probe (6) descend within the tube (2).

The vertically downward translation of the probe (6) terminates shortly after the forked inlets (11) contact the periapical region (5) of the test tube (2). In the preferred mode, force is exerted against the probe (6) as it contacts the periapical region (5) so as to cause the probe (6) to slide to its lowest contact point with the periapical region (5). This causes the probe (6) to become centered over the apical region (4). A spring biase or other biasing means may be employed for exerting this force. After meniscus has been lowered to the periapical region (5), the aspiration may be terminated.

After the prewash liquid (7) has been evacuated as indicated above, the pellet may be dislodged and resuspended by the application of a wash liquid (7). In the preferred mode, the wash liquid (7) contains a low level of surfactant. The pellet may be dislodged by directing the expression of wash liquid (7) with force onto central region of the pellet. Recall that the centering of the probe (6) positioned the outlet (12) of the liquid channel (8) directly over the pellet, i.e. the apical region (4). Furthermore, recall that contact of the forked inlets (11) with the periapical region (5) prevents direct contact between the outlet (12) of the liquid channel (8) and both the pellet and the meniscus. It is important not to contaminate the outlet (12) with prewash liquid (7) or with magnetic particles (1) as this could lead to cross contamination if the probe (6) is employed with other test tubes (2).

As wash liquid (7) is expressed into the test tube (2), the probe (6) is translated vertically upward. The vertically upward translation of the probe (6) proceeds at a speed which allows the forked inlets (11) and the outlet (12) to always be proximal to but above the rising surface level of the wash liquid (7) within the test tube (2). The optimal quantity of wash liquid (7) to be expressed into the test tube (2) will depend upon the particular application.

Expression of wash liquid (7) with force onto the pellet can create foam, particularly if the wash liquid (7) includes surfactant. The presence of this foam can impede the subsequent magnetic sedimentation of the magnetic particles (1). The wash liquid (7) may be defoamed by drawing air through the test tube (2). One method to do this is to draw air through the forked inlets (11). This air circulation causes the liquid (7) to defoam and allows the magnetic sedimentation to proceed at its usually rate.

Since the test tube (2) is still mounted within its magnetic rack, the resuspended magnetic particles (1) will begin to magnetically sediment as soon as the mixing of the suspension is stopped by terminating the expression of wash liquid (7) into the test tube (2).

After the magnetic sedimentation is complete and the pellet has reformed once again, the wash liquid (7) may again be evacuated from the test tube (2). As before, the probe (6) is lowered into the test tube (2) while vacuum source is activated so as to cause the wash liquid (7) to be aspirated into the forked inlets (11). The aspiration of the wash liquid (7) may be performed in the same manner as the aspiration of the prewash liquid (7).

The above washing protocol may be repeated as often as desired.

If an array of probes (6) are attached to a manifold type apparatus, an entire array of test tubes (2) within a magnetic rach may be washed simultaneously. If the probes (6) are attached to an X-Y-Z positioner, the probes (6) may be horizontally translated so as to serially wash several racks of test tubes (2).

What is claimed is:

1. A probe employed in conjunction with an apparatus for washing a pellet of magnetic particles, the pellet being magnetically bound to an apical region at the bottom of a vessel, the bottom of the vessel including a periapical region adjacent to and above the apical region, the probe comprising:
   a liquid channel terminating with an outlet for expressing liquid onto the pellet within the vessel, and
   a vacuum channel terminating with a forked inlet for aspirating liquid from the vessel,
   said liquid channel and said vacuum channel being adjacent to one another and coupled to one another,
   said forked inlet having at least two prongs with a configuration for contacting the periapical region of the vessel and for avoiding contact with the apical region of the vessel.

2. A probe as described in claim 1 wherein:
   said configuration of said forked inlet for serving to position said outlet over the pellet, i.e. over the apical region of the vessel.

3. A probe as described in claim 2 wherein:
   said outlet having a length for avoiding contact with the pellet when said outlet is positioned over the apical region of the vessel by means of said forked inlet.

4. A probe as described in claim 1 wherein:
   said vacuum channel including two or more subchannels, each of said subchannels terminating with one prong of said forked inlet.

5. An apparatus for washing a plurality of pellets of magnetic particles, each pellet being magnetically bound to an apical region at the bottom of one of a corresponding plurality of vessels, the bottom of each vessel including a periapical region adjacent to and above the apical region, the apparatus comprising:
   a plurality of liquid channels, each of said liquid channels terminating with an outlet for expressing liquid onto the pellet within one of the vessels, and
   a plurality of vacuum channels, each of said vacuum channels terminating with a forked inlet for aspirating liquid from one of the vessels,
   each of said plurality of liquid channels corresponding to one of said plurality of vacuum channels, said corresponding liquid channels and vacuum channels being adjacent to and coupled to one another,
   each of said forked inlets having at least two prongs with a configuration for contacting the periapical region of one of the vessels and for avoiding contact with the apical region of the vessels.

6. An apparatus as described in claim 5 wherein:
   said configuration of each of said forked inlets for serving to position said outlet over the pellet, i.e., over the apical region of the vessel,
   said outlet having a length for avoiding contact with the pellet when said outlet is positioned over the apical region of the vessel by means of said forked inlet.

7. An apparatus as described in claim 5 wherein:
   said vacuum channel including two or more subchannels, each of said subchannels terminating with one prong of said forked inlet.

* * * * *